United States Patent [19]

Oberhardt et al.

[11] Patent Number: 4,843,017
[45] Date of Patent: Jun. 27, 1989

[54] DEVICE FOR THE SEPARATION OF THE LIGHTER FRACTION FROM THE HEAVIER FRACTION OF A LIQUID SAMPLE

[75] Inventors: Bruce J. Oberhardt, Raleigh; Phyllis J. Palmer, Durham, both of N.C.

[73] Assignee: Becton, Dickinson and Company, Franklin Lakes, N.J.

[21] Appl. No.: 113,577

[22] Filed: Oct. 27, 1987

Related U.S. Application Data

[62] Division of Ser. No. 694,717, Jan. 25, 1985.

[51] Int. Cl.$^4$ ............................................... G01N 1/18
[52] U.S. Cl. .................................... 436/177; 436/178;
422/101; 422/104; 210/321.6; 210/321.84;
210/433.1; 210/649; 128/762; 128/763;
128/764; 604/414
[58] Field of Search ................ 422/101, 104; 436/177,
436/178; 210/247, 321.6, 321.84, 433.1, 649;
128/760, 762, 763, 764; 604/414

[56] References Cited

U.S. PATENT DOCUMENTS 4,639,316 1/1987 Eldegheidy ..................... 210/416.1

*Primary Examiner*—Barry S. Richman
*Assistant Examiner*—Lynn M. Kummert
*Attorney, Agent, or Firm*—John L. Voellmicke

[57] ABSTRACT

A device for the separation of a lighter fraction from the heavier fraction of a liquid sample for use with two evacuated receptacles includes a housing having an interior cavity and a membrane separator dividing this cavity into a first portion and a second portion. The membrane separator has a porosity selected for the desired separation thereacross. An inlet structure is provided for fluid communication between the first portion of the interior cavity and the source of the liquid sample. First structure is provided to allow fluid communication between the first portion of the interior cavity and the first evacuated receptacle. This first structure is opposed from the inlet structure so that liquid passing from the inlet to the first structure travels in a direction along the surface of the membrane. Further structure is provided to allow fluid communication between the second portion of the interior cavity and the second evacuated receptacle.

5 Claims, 11 Drawing Sheets

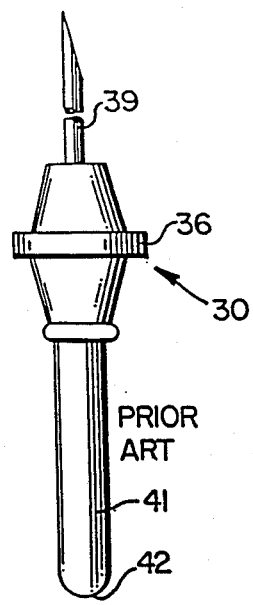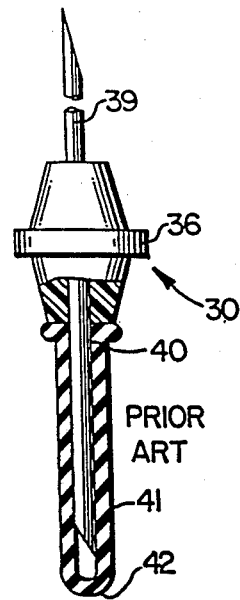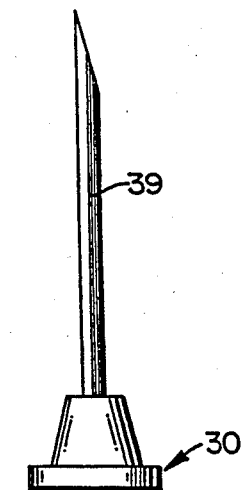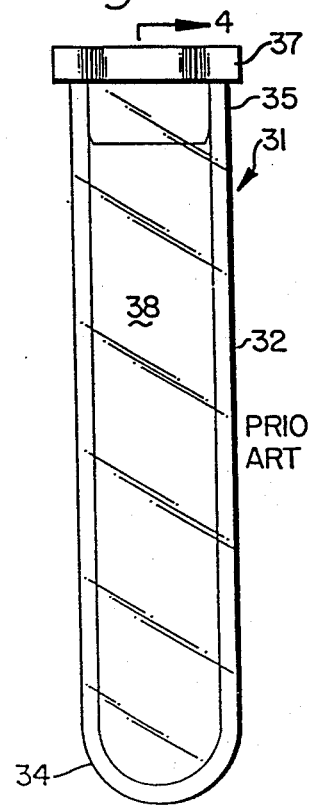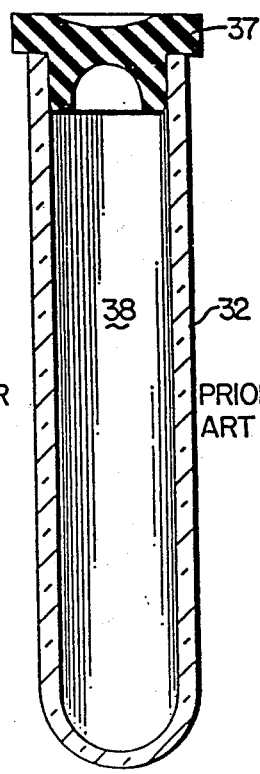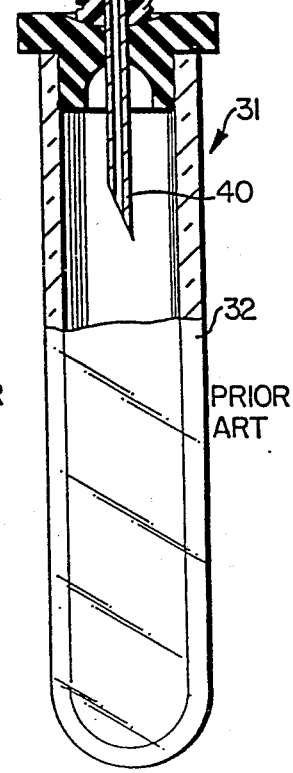
Fig. 1  Fig. 2
Fig. 3  Fig. 4  Fig. 5

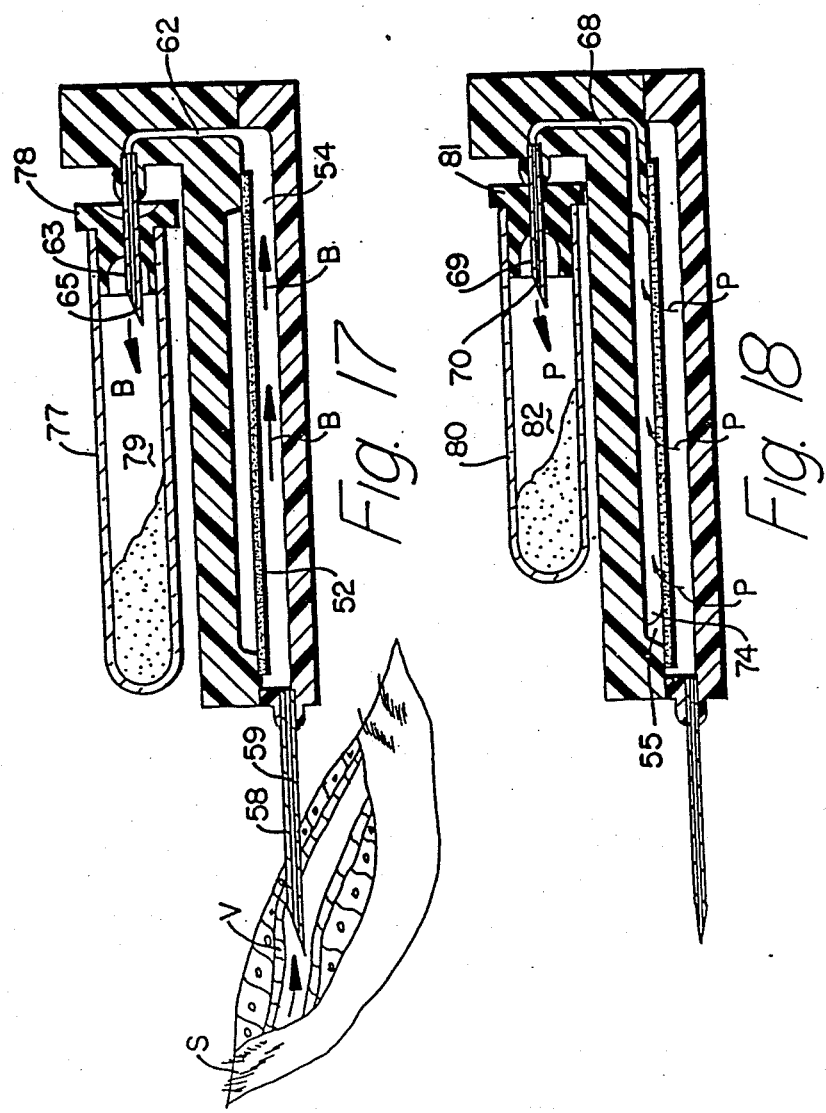

DEVICE FOR THE SEPARATION OF THE LIGHTER FRACTION FROM THE HEAVIER FRACTION OF A LIQUID SAMPLE

This is a division of application Ser. No. 694,717, filed 1-25-85.

BACKGROUND OF THE INVENTION

1. Field of the Invention.

The present invention relates to devices for separating the lighter fraction from the heavier fraction of a liquid sample. More particularly, this invention relates to self-contained devices for separation of the liquid component from the cellular component of a blood sample without the use of a centrifuge, an auxiliary circulating system, an auxiliary pump or the like.

2. Description of the Prior Art.

A common method of obtaining a blood sample involves the use of a two-cannula needle assembly and an evacuated glass tube having a pierceable stopper. The method involves inserting one cannula of the needle assembly into the subject's vein and piercing the stopper of the evacuated glass tube with the other cannula of the needle assembly, thereby establishing fluid communication between the vein and the interior of the glass tube. Due to the lower pressures within the evacuated glass tube blood is drawn from the subject into the tube. Evacuated tubes and needle assemblies for use therewith are described in U S. Pat. No. 3,469,572 to Nehring. Such devices are commercially available under the VACUTAINER Brand name from Becton, Dickinson and Company, Paramus, N.J.

The blood sample, in the evacuated glass tube, may then be placed in a centrifuge and centrifuged until the more dense cellular component of the blood sample is driven to the bottom of the tube and the less dense plasma is positioned at the top of the sample. The stopper from the tube may then be removed and the plasma sample poured off for subsequent testing. If serum is desired the blood sample is allowed to clot before centrifuging the blood sample.

U.S. Pat. No. 4,057,499 to Buono teaches the collection of a plasma or serum sample using a sampling member having a hollow interior for the collection of liquid and a piston connected to one end of the sampling member. The piston includes a lip for forming a seal with the interior walls of the sample containing glass tube and an interior portion contains a filter and a one-way valve. In use, a blood sample, in a glass tube, is centrifuged to separate the liquid and the cellular phases and then the device of Buono is placed in the tube and forced along the inner tube surface so that the piston passes through the liquid portion of the sample forcing the liquid portion through the filter and through the valve into the hollow interior of the device. The device containing a portion of the liquid sample is then removed from the glass tube. Buono teaches that it is desirable to physically separate the liquid phase of the sample from the cellular phase to prevent deleterious chemical interaction between the two. Accordingly, Buono teaches the use of a centrifuge and a separate filtering apparatus to obtain the plasma or serum sample.

It is believed that forcing a filter membrane through a blood sample, without the use of a centrifuge, is not a practical method of separating the liquid and the cellular components because the filter membrane would soon become caked with the cellular components and unable to perform its task as a filter. Accordingly, it is believed that if the liquid phase of the blood sample is to be filtered from the cellular portion of the blood sample, without the use of a centrifuge, a cross-flow filter arrangement should be provided. In a cross-flow arrangement, the blood sample flows across the surface of the filter membrane in a direction parallel to the major axis of the membrane while a secondary force provides a pressure differential between the blood side of the membrane and the liquid side so that the liquid phase will pass through the membrane. U.S. Pat. Nos. 3,211,645; 4,191,182; 4,212,742 and 4,343,705 teach various devices for the filtration of liquid using a cross-flow technique. In each of these patents, the devices utilized require an applied pressure driving force from a separate source across the membrane filter in order to bring about the proper separation. That is, a separate pumping and/or circulating device must be used in conjunction with the cross-flow filter.

It is believed that the cross-flow method of filtration is superior because when the blood sample is caused to flow in parallel relationship across the filter membrane there is substantially less tendency for the membrane to be clogged by the cellular portion of the blood sample and therefore allowing the blood to be filtered without the use of a centrifuge. In any event, all of the devices and methods described above require the use of relatively expensive support devices such as a centrifuge, liquid pumping and/or circulating systems, or the like. In addition, dependency on additional equipment can consume valuable time in emergency situations wherein the liquid phase of the patient's blood sample must be analyzed properly in order to diagnose the problem and/or to provide proper emergency treatment. In these situations, it is desirable to provide a device for the separation of the liquid phase of the blood sample from the cellular phase immediately upon the drawing of the blood sample without further steps.

The prior art teaches various devices and methods to separate the liquid phase from the cellular phase of a blood sample. All of the above-mentioned prior art devices require the use of a centrifuge or auxiliary pumping or circulating systems to provide the liquid phase sample. There is still a need for a simple, straightforward, reliable, easily fabricated device for the separation of the lighter fraction from the heavier fraction of a liquid sample which will operate without the use of additional equipment such as centrifuges and pumps, to promptly produce an isolated quantity of the lighter fraction of the liquid sample.

SUMMARY OF THE INVENTION

The device for the separation of the lighter fraction from the heavier fraction of a liquid sample for use with two evacuated receptacles, a first evacuated receptacle and a second evacuated receptacle, includes a housing having an interior cavity and a membrane separator dividing the interior cavity into a first portion and a second portion. The membrane separator has a porosity selected for the desired separation thereacross. Also included is inlet means for providing fluid communication between the first portion of the cavity and the source of the liquid sample and first communication means for providing fluid communication between the first portion of the cavity and the first evacuated receptacle. This first communicating means is opposed from the inlet means so that liquid passing from the inlet means to the first communication means travels in a direction along the surface of the membrane. Also included is a second communication means for providing fluid communication between the second portion of the interior cavity and the second evacuated receptacle.

In accordance with another embodiment of the present invention a device for separation of plasma from a blood sample for use with two rigid evacuated receptacles wherein each receptacle includes an open end and a pierceable stopper sealing the open end includes a housing having an interior cavity and a membrane separator dividing the cavity into a first blood receiving portion and a second plasma receiving portion. This membrane separator has a pore size within the range of between about 0.2 micron and 1.5 microns. Also included is inlet means for providing fluid communication between the blood receiving portion and the source of the blood sample and first communication means for providing fluid communication between the blood receiving portion and the first evacuated receptacle. The first communication means is opposed from the inlet means so that blood passing from the inlet means to the first communication means travels in a direction along the surface of the membrane. The first communication means includes a first needle cannula having a lumen therethrough for piercing the stopper of the first evacuated receptacle to establish fluid communication therewith. Second communication means for providing fluid communication between the plasma receiving portion and the second evacuated receptacle includes a second needle cannula having a lumen therethrough for piercing the stopper of the second evacuated receptacle to establish fluid communication therewith so that when the inlet means is in fluid communication with the source of the blood sample and the first communication means is in fluid communication with the first evacuated receptacle, and the second communication means is in fluid communication with the second evacuated receptacle, the blood sample flows through the inlet means along the membrane through the first communication means into the first evacuated receptacle, simultaneously, plasma is drawn through said membrane and said second communication means into the second evacuated receptacle.

In accordance with the principles of the present invention, a number of advantages are achieved. Primarily, the present invention provides a simple, straightforward, reliable, easily fabricated device for the separation of the lighter fraction from the heavier fraction of a liquid sample which will operate without the use of additional equipment such as centrifuges and pumps, to promptly produce an isolated quantity of the lighter fraction of the liquid sample. Also, the present invention provides greater flexibility in optimizing the efficiency of the separation process by allowing the use of two separate evacuated receptacles which may be varied as to size and degree of evacuation.

BRIEF DESCRIPTION OF THE DRAWINGS

FIG. 1 is a side elevation view representing a known blood collection needle assembly;

FIG. 2 is a partial cross-sectional view of the needle assembly of FIG. 1 illustrating the second cannula and the internal structure of the resilient sleeve;

FIG. 3 is a side elevation view of a known and used evacuated blood collection tube;

FIG. 4 is a cross-sectional view of the evacuated tube of FIG. 3 taken along line 4—4;

FIG. 5 is a partial cross-sectional view illustrating the interaction between the needle assembly of FIG. 1 and the evacuated tube of FIG. 3 when the second cannula of the needle assembly pierces the stopper of the evacuated tube;

FIG. 17 is a partial cross-sectional view of the device of FIG. 15 taken substantially along line 17—17;

FIG. 18 is a cross-sectional view of the device of FIG. 15 taken along line 18—18;

DETAILED DESCRIPTION

Figure 6:
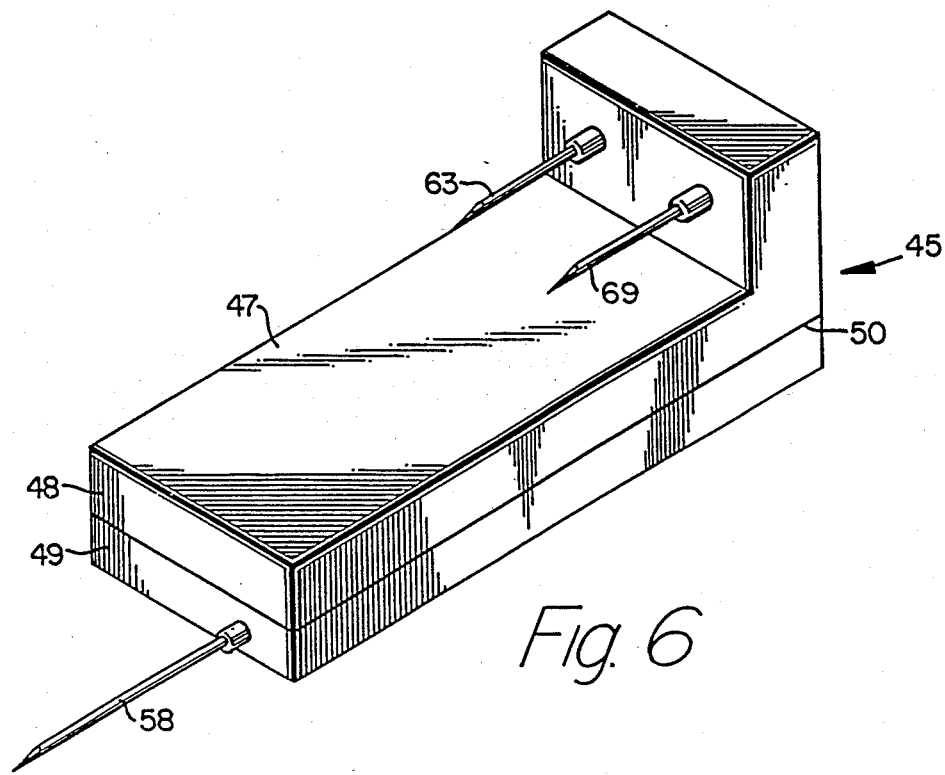
FIG. 6 is a perspective view of a preferred embodiment of the device for separation of plasma from a blood sample of the present invention.
Figure 7:
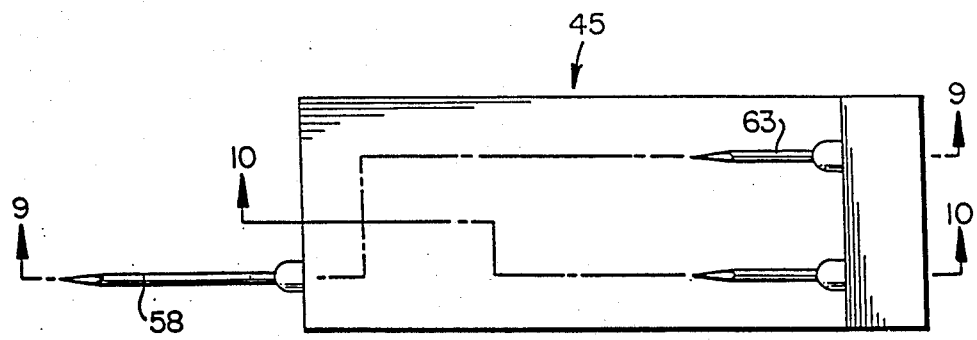
FIG. 7 is a top plan view of the device of FIG. 6.
Figure 8:
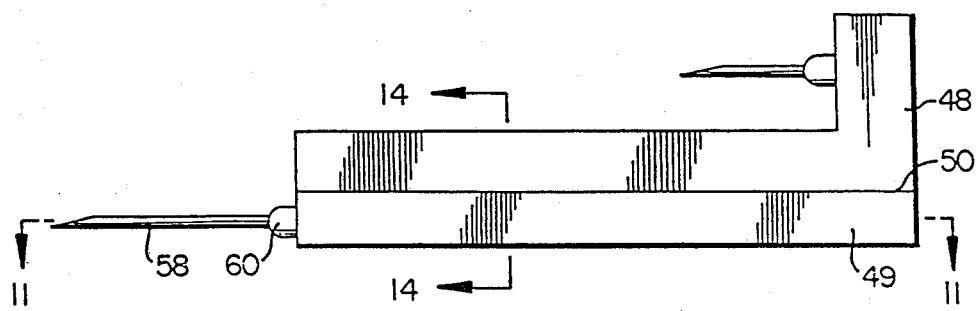
FIG. 8 is a side elevation view of the device of FIG. 6.
Figure 9:
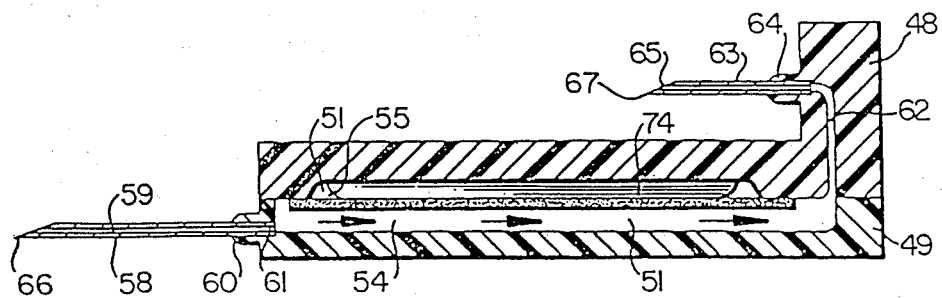
FIG. 9 is a cross-sectional view of the device of FIG. 7 taken along line 9—9.
Figure 10:
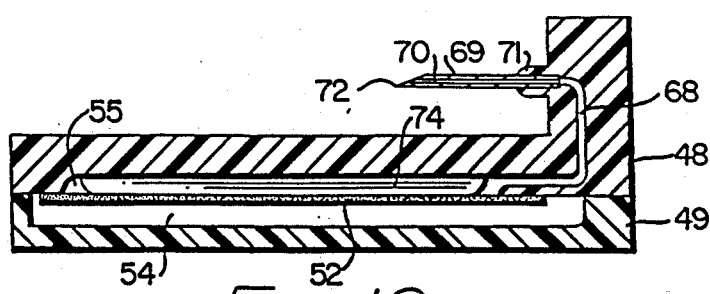
FIG. 10 is a cross-sectional view of the device of FIG. 7 taken along line 10—10.
Figure 11:
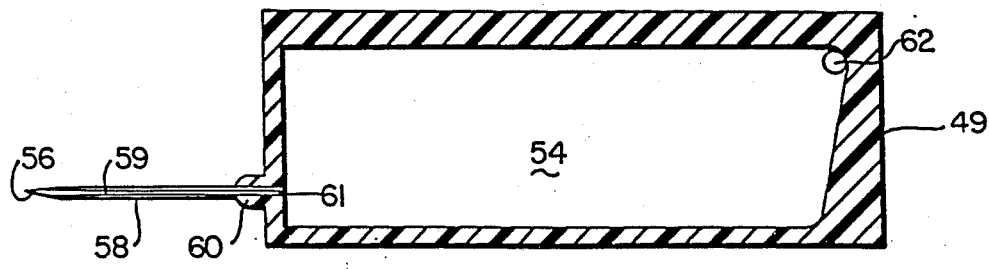
FIG. 11 is a cross-sectional view of the device of FIG. 8 taken along line 11—11.
Figure 12:
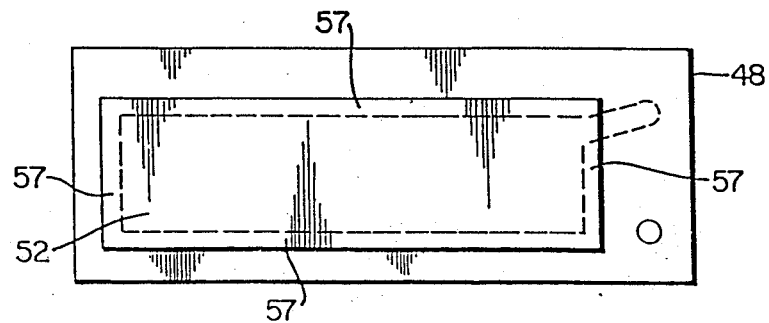
FIG. 12 is a bottom plan view of the upper housing portion of the device of FIG. 6 illustrating the membrane separator attached to the upper housing portion.
Figure 13:
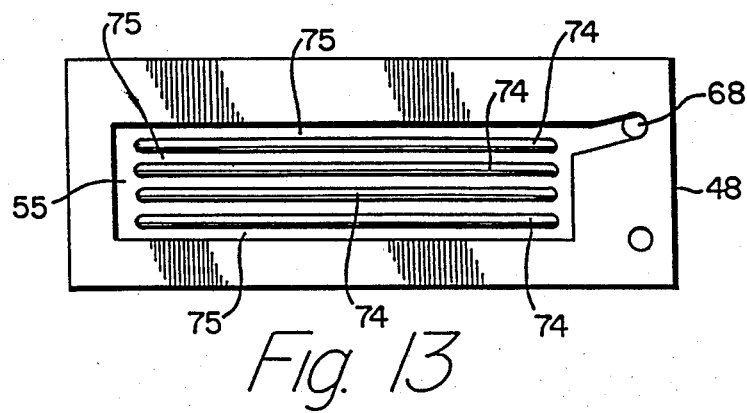
FIG. 13 is a bottom plan view of the upper housing portion of the device of FIG. 6, similar to the view of FIG. 12 but without the membrane separator.
Figure 14:
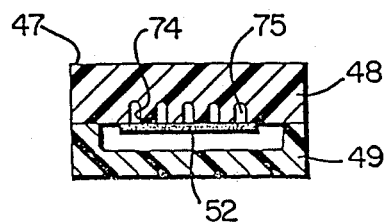
FIG. 14 is a cross-sectional view of the device of FIG. 8 taken along line 14—14.
Figure 15:
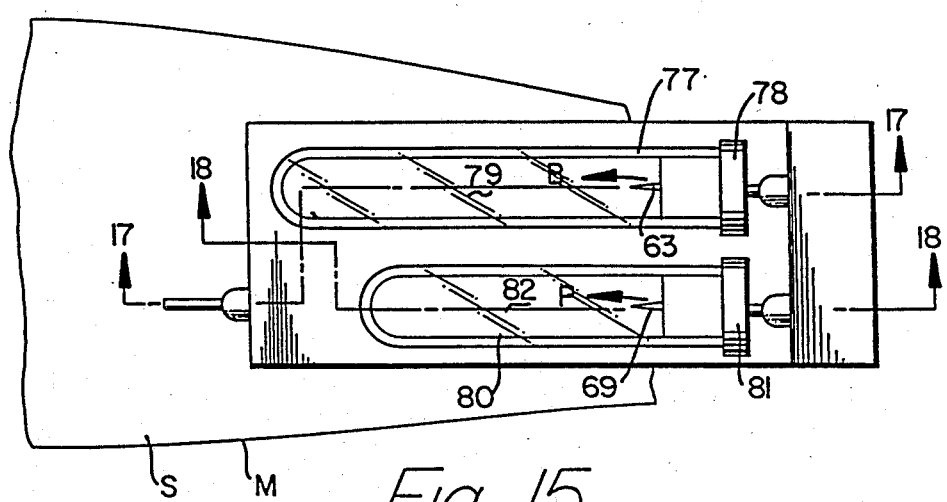
FIG. 15 is a top plan view of the device of FIG. 6 in use with evacuated tubes, taking a blood sample.
Figure 16:
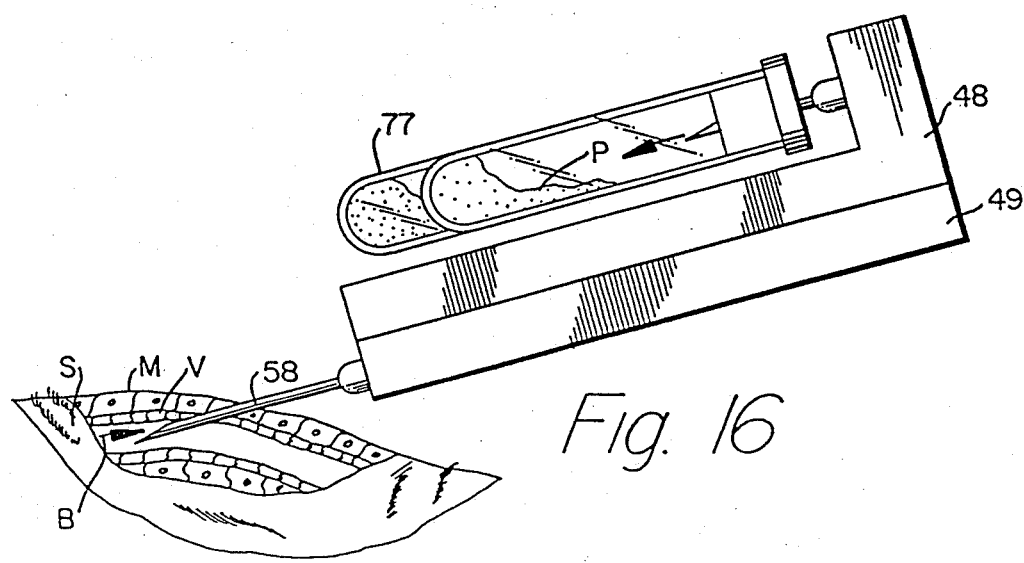
FIG. 16 is a side elevation view of the device of FIG. 15, in use taking a blood sample.
Figure 19:
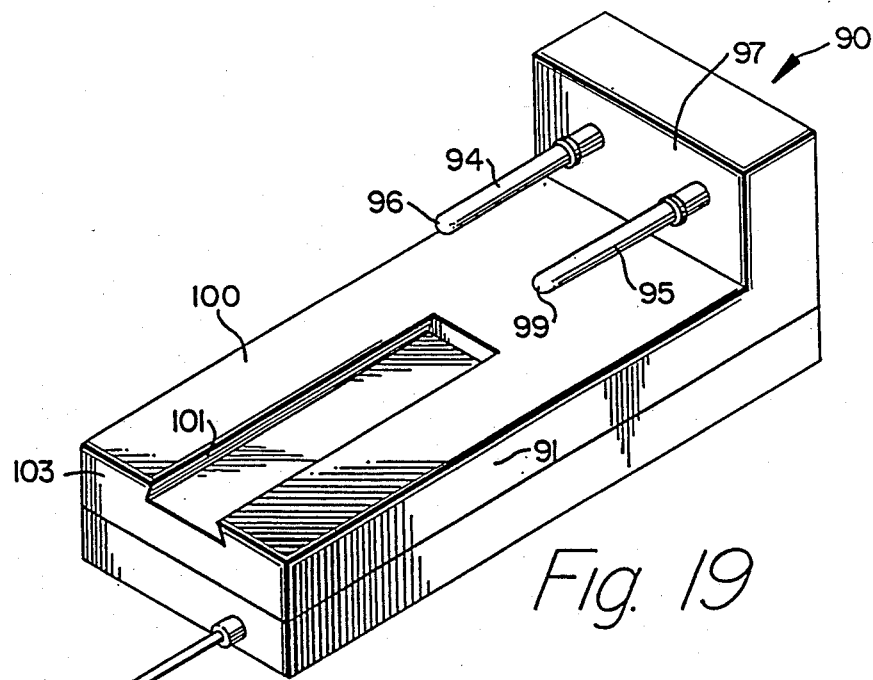
FIG. 19 is a perspective view of another embodiment of the preferred device for separation of plasma from a blood sample.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1–5, known prior art blood collection devices include a blood collection needle 30 and a blood collection evacuated glass tube 31. The blood collection tube includes a cylindrical glass body 32 with closed end 34 and neck portion 35. The neck portion is sealed by a resilient pierceable stopper 37 which is applied to the tube while both components are in a reduced pressure environment so that the interior portion 38 has an absolute internal pressure less than atmospheric pressure.

The blood collection needle includes a hub 36, a first cannula 39 adapted to pierce a patient's flesh and enter a blood containing vein therein. Second cannula 40 is adapted to pierce stopper 37 to establish fluid communication between the patient's vein and the interior of the evacuated glass tube so that a blood sample is drawn from the patient into the tube. The first cannula and second cannula of the blood collection needle may be separate cannulas in fluid communication with each other through the hub or they may be part of one cannula which passes through the hub. Some blood collection needles include a resilient sleeve which prevents blood from leaving the blood collection needle after venipuncture. A resilient sleeve 41 includes a closed end 42 which is adapted to be pierced by second cannula 40 upon the application of external force to the sleeve in the direction along longitudinal axis of cannula 40. This force can be applied by forcing the blood collection tube stopper onto the second cannula, as best illustrated in FIG. 5. After the blood sample is taken, the evacuated tube is removed from the blood collection needle and the resilient sleeve returns to its original position which allows it to prevent further blood from leaving the blood collection needle. It can be seen that this type of needle assembly will allow several tube samples to be taken from the same venipuncture because the second cannula is sealed after each tube is removed therefrom. Blood collection needle hubs commonly have external threads (not shown) to interact with a tube holder (not shown) to facilitate guiding the tube toward the second cannula so that the cannula pierces the central, thinner, portion of the stopper.

The blood sample, in the evacuated tube, may be placed in a centrifuge (not shown) and spun until the more dense cellular component of the blood sample is driven to the closed end portion of the tube and the less dense plasma is positioned above the cellular component closer to the neck portion. The stopper from the tube may then be removed and the plasma poured off for subsequent testing. Also, serum may be obtained by allowing the blood sample to coagulate before centrifuging the blood sample. The serum or plasma produced is used in various types of blood testing equipment which analyze the contents thereof to provide data with respect to the state of the patient's blood.

Referring now to FIGS. 6-14, a preferred device 45 for separation of plasma from a blood sample for use with two evacuated receptacles, such as the blood collection evacuated glass tubes hereinabove described, includes housing 47 comprising upper housing portion 48 and lower housing portion 49 joined along line 50 to form an interior cavity 51.

A membrane separator 52 divides interior cavity 51 into a first blood receiving portion 54 and a second plasma receiving portion 55. Membrane separator 52 is attached to upper housing portion 48 along sealing area 57 of the upper housing portion, via heat sealing, ultrasonic welding, solvent adhesive or other suitable means, so that fluid passing from blood receiving portion 54 to plasma receiving portion 55 must pass through membrane separator 52. It will be apparent to one skilled in the art that there are numerous constructions which will allow the separation of housing portions by a membrane, for example, clamping the membrane between the housing portions, and that the structure recited hereinabove is exemplary of these many possibilities.

An injection cannula 58 having a lumen 59 therethrough is attached to a hollow hub portion 60 of the lower housing portion via adhesive or other suitable means. Lower housing portion 49 also includes an inlet conduit 61 providing fluid communication between lumen 59 and blood receiving portion 54. The injection cannula includes a sharpened distal tip 56 adapted to pierce the subject's flesh and enter a vein therein to provide the blood sample. It is within the purview of the present invention to include a structure wherein the injection cannula is separated from the housing portion by a length of flexible tubing so that the housing portion need not be positioned at the injection site but may be conveniently placed closely thereto. A blood communication conduit 62 communicates between blood receiving portion 54 and upper housing portion 48. The blood communication conduit is opposed from inlet conduit 61 so that blood passing from the inlet conduit to the blood communicating conduit travels in a direction along the length of membrane separator 52 to establish a cross-flow relationship between the blood and the membrane. A first needle cannula 63 is mounted in the upper housing portion at hub 64 via adhesive or other suitable means. Cannula 63 includes lumen 65 which is in fluid communication with blood communication conduit 62. First needle cannula 63 also includes sharpened tip 67 adapted to pierce the stopper of an evacuated blood collection tube.

A second needle cannula 69 having a lumen 70 therethrough is attached to a second hub portion 71 of the upper housing portion via adhesive or other suitable means. The second needle cannula includes a sharpened tip 72 adapted to pierce the stopper of an evacuated blood collection tube. The upper housing portion also includes a plasma communication conduit which allows fluid communication between the lumen of the second needle cannula and plasma receiving portion 55 of the housing.

In order to support membrane 52 when vacuum forces are applied, as will be explained in more detail hereinafter, support ribs 74 are provided in plasma receiving portion 55 of the upper housing. In the preferred embodiment these ribs are arranged in a parallel arrangement with recesses 75 adjacent to the support ribs for allowing the flow of plasma from the membrane to plasma communication conduit 68. In the preferred embodiment the ribs are formed integrally with the upper housing portion. It is within the purview of the present invention to include other structures to support the membrane against the vacuum forces. These other structures include, but are not limited to: a separate panel, having raised surfaces, inserted in the upper housing portion; a structural screen supporting the membrane; and structural material laminated to the membrane and heat sealed to the housing portion.

FIGS. 15-18 depict the preferred device for the separation of plasma from a blood sample in use. Initially, injection cannula 58 is inserted through the skin S of a mammalian body M so that lumen 59 thereof is in fluid communication with the blood B in vein V. Immediately after the fluid communication with the vein is established, a rigid evacuated blood collection tube 77 having a pierceable stopper 78 is guided along upper housing portion 48 so that first needle cannula pierces stopper 78 so that there is fluid communication between interior 79 of the blood collection tube and the lumen of cannula 63. Simultaneously, a rigid evacuated collection tube 80 is guided along upper housing portion 48 so that second needle cannula 69 pierces a stopper 81 of the evacuated collection tube and there is fluid communication between interior 82 and the lumen of cannula 69.

It should be noted that it is desirable that evacuated blood collection tube 77 and evacuated blood collection tube 80 should be guided onto the device substantially simultaneously so that fluid communication between the respective cannulas and tubes is substantially simultaneous. When using a membrane having large pores, the simultaneous connection of the tubes avoids the possibility that one tube, inserted without the other, will lose a small portion of its vacuum force by drawing some environmental air through the membrane before the blood covers the membrane. This potential problem can also be avoided by pre-wetting the membrane with glycerol, saline solution or the like.

With the evacuated tubes connected to the device, as best illustrated in FIGS. 17 and 18, evacuated blood collection tube 77 creates a vacuum force within the housing which draws blood from vein V through lumen 59 of cannula 58, through blood receiving portion 54 along the surface of membrane 52 and, finally, through blood communicating conduit 62, lumen 65 of needle cannula 63 and into the blood collection tube. At the same time that the blood collection tube is drawing blood through the device, evacuated collection tube 80 is providing a vacuum force on the side of membrane 52 opposite from the blood supply. The vacuum force created by collection tube 80 causes plasma from the stream of blood flowing through blood receiving portion 54 to cross through membrane 52 into plasma receiving portion 55 of the housing. The plasma is guided along the housing by support ribs 74, through plasma communication conduit 68 and the lumen of second needle cannula 69 into collection tube 80.

When the pressure inside the collection tubes is approximately equal to the blood pressure of the subject, evacuated collection tube 80 will contain a quantity of plasma, separated from the blood, ready for use. Further, blood collection tube 77 will contain a quantity of blood, still containing plasma, which may be held aside pending the outcome of the analysis of the plasma from tube 80. An advantage of the present invention is that it produces samples in two separate tubes. Accordingly, each tube can be sent to a different physical area for storage and/or testing as opposed to separation processes where the plasma and the remaining portion of the blood are contained in the same tube. Also, an important feature of the instant invention is that it allows the use of two separate vacuum sources, thus allowing the use of a wide variety of evacuated tubes having various volumes and degrees of evacuation. This feature greatly increases the flexibility of the instant invention with respect to optimizing the efficiency of the separation process. For example, differential pressure across the membrane can be varied using evacuated tubes having different degrees of evacuation. This is an advantage over systems driven by a single source of vacuum or pressure.

Membrane separator 52 is constructed so that it contains pores having a diameter selected so that plasma from a blood sample can flow through the membrane while the cellular components of the blood sample are too large to pass therethrough. It is desirable to use a membrane having a pore size within the range of between about 0.2 micron and 1.5 microns. It is preferred that the membrane has a pore size within the range of between about 0.4 micron and 0.6 micron.

If additional plasma or serum is required, depending on the time element, blood collection tube 77 may be spun, in a centrifuge, to provide this additional fluid. Accordingly, a blood collection tube containing anticoagulant may be chosen so that the blood sample does not clot and plasma may still be obtained. Also, a blood collection tube containing a separator gel may be used. This latter type of tube may be centrifuged immediately, causing the gel to move to a position between the cellular mass and the plasma, thus preserving the sample for later use.

In the preferred device injection cannula 58, first needle cannula 63 and second needle cannula 69 can be chosen from the range of size of commercially available blood collection needles. It is preferred that injection cannula 58 be within the range of about 20 gauge to 22 gauge and have a length within the range of about one inch to 1.5 inches (25 mm to 38 mm). The first and second needle cannula are preferably within the range of about 20 gauge to 22 gauge and having a length of about 0.635 inches (16 mm).

A wide range of membrane sizes can be used with the present invention, depending on the variables associated with the various other elements. With respect to plasma separation, a membrane having an area within the range of about 11 $cm^2$ to 32 $cm^2$ is desirable when using commercially available evacuated tubes. In the preferred embodiment the membrane separator is sized so that approximately 11 $cm^2$ of area is available for transfer of plasma from the blood receiving portion 54 to plasma receiving portion 55. Also, it is desirable that the ratio of length to width be in the range of about 4/1 to 10/1. It should be noted that the volume of the empty space within the interior cavity of the housing, the inlet conduit, the blood communication conduit and the plasma communication conduit must be held to the lowest possible practical value to minimize the amount of air that will be drawn into the evacuated tubes in order to fill this empty space with blood or plasma. This air, when it enters the evacuated tubes, reduces the amount of vacuum force available for drawing and separating the blood sample.

Although the preferred embodiment is described using a membrane suitable for separating plasma from whole blood, it is within the purview of the instant invention to include embodiments suitable for separating light and heavy components of other fluids, such as separating a liquid portion from a colloidal suspension or separating small molecular species from a blood sample. Accordingly, membranes such as known ultrafiltration membranes and known non-woven membranes having suitable pore ratings may be used as components of the instant invention for separating the light and heavy components of a liquid sample.

Referring now to FIGS. 19–22, an alternative embodiment of the present device for separation of plasma from a blood sample 90 functions in a substantially similar manner as the embodiment hereinabove described but includes additional features. A housing 91 includes injection cannula 92, first needle cannula (not shown) covered by first resilient sleeve 94, and second needle cannula (not shown) covered by second resilient sleeve 95. Sleeve 94 includes closed end 96 which is adapted to be pierced by the first injection cannula upon the application of external force to the sleeve in a direction along the cannula toward upright wall 97 of the housing to allow fluid passage through the first needle cannula. Sleeve 94 will return to its original position upon termination of the external force. Likewise, second resilient sleeve 95 includes closed end 99 which is adapted to be pierced by the second needle cannula upon the application of an external force to the second resilient sleeve along the second needle cannula in a direction toward upright wall 97, thus allowing fluid passage through the second needle cannula. Second resilient sleeve will return to its original position upon termination of the external force.

Housing 91 includes planar surface 100 having dove-tail guide groove 101 formed therein. It should be noted, in this embodiment, the first needle cannula and the second needle cannula are positioned in a substantially parallel relationship. Further, dove-tail groove 101 originates at end 103 of the housing and runs along planar surface 100 in a direction which is substantially parallel to the longitudinal axes of the first and second needle cannula.

Figure 20:
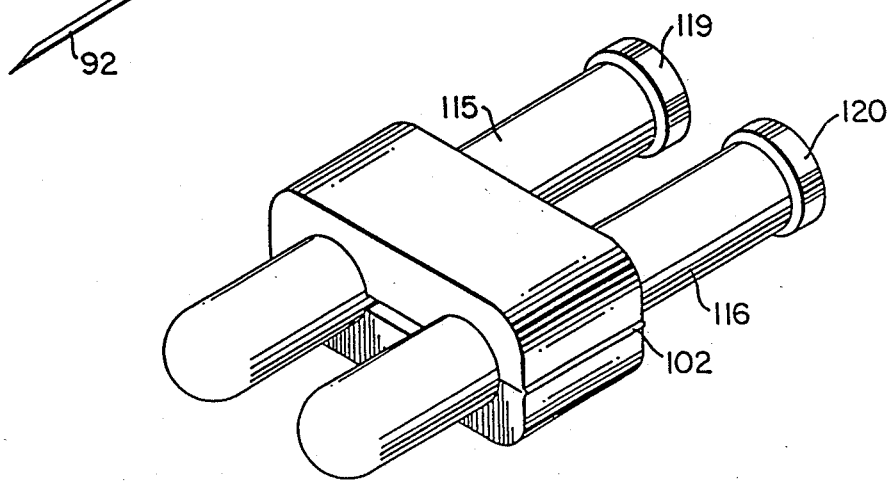
FIG. 20 is a perspective view of a holding clamp, with two evacuated tubes, for use with the device of FIG. 19.
Figure 21:
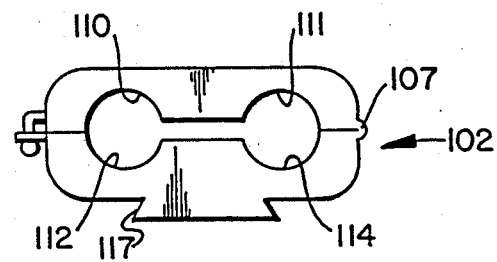
FIG. 21 is an end elevation view of the holding clamp of FIG. 20 illustrated without the evacuated tubes.
Figure 22:
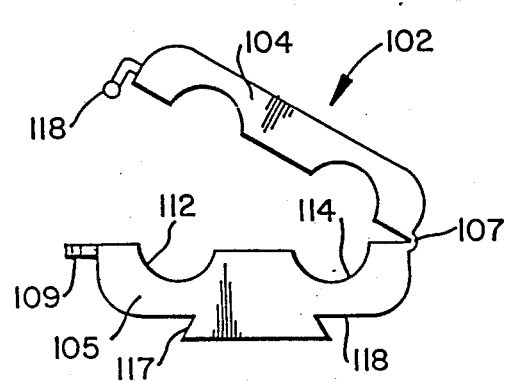
FIG. 22 is an end elevation view of the holding clamp of FIG. 21 illustrated in an open position.

Also included in this embodiment is holding clamp 102 for releasably holding evacuated tubes 115 and 116 having resilient stoppers 119 and 120, respectively. Clamp 102 includes upper portion 104 and lower portion 105 joined at a hinge 107. The upper portion of the holding clamp includes locking pin 108 which is adapted to engage aperture 109 in the lower portion. Locking pin 108 engages aperture 109 in a snap-fit locking arrangement so that force is required for disengagement. Upper portion includes circularly shaped recesses 110 and 111 having a coordinated relationship with circularly shaped recesses 112 and 114 in the lower portion so that when evacuated tubes 115 and 116 are placed in recesses 112 and 114 and the upper portion is hinged shut so that locking pin 108 engages aperture 109, the tubes will be held in a parallel relationship, as best illustrated in FIG. 20.

Holding clamp 102 also includes dove-tail guide projection 117 projecting outwardly from bottom surface 118 of lower portion 105. Dove-tail guide projection 117 is adapted to cooperatively engage dove-tail guide groove 101 and slide freely therein. In using the instant embodiment the operator places evacuated tubes in holding clamp 102 and closes the locking clamp so that the tubes are held therein. The operator then engages the dove-tail guide projection of holding clamp 102 into the dove-tail guide groove 101 of the housing and slides the clamp toward the needle cannula but does not allow the cannula to pierce the stoppers of the evacuated tubes. At this point, the injection cannula is inserted into the subject to achieve venipuncture and the holding clamp is moved in a direction toward upright wall 97 of the housing to cause the needle cannula to pierce resilient sleeves 94 and 95 and the resilient stoppers 119 and 120 to cause fluid communication between the evacuated tubes and the needle cannula.

It may be desirable to only form the dove-tail groove in an area near the first and second needle cannula and to provide an enlarged entrance means at the end of the groove furthest from the cannula, so that the dove-tail guide projection of the clamp may be engaged in the dove-tail groove at a point intermediate the ends of the planar surface rather than at the end thereof.

The holding clamp of the instant embodiment allows the evacuated tubes to be clamped in a parallel relationship and guided toward the injection cannulas so that both resilient stoppers will be pierced by the respective cannula simultaneously. The instant embodiment also provides resilient sleeves to prevent fluid from passing through the injection cannula. It should be noted that these features, are independent features and are not dependent on each other for function. Accordingly, it is also within the purview of this invention to provide a device having either the resilient sleeves or a holding clamp with guiding means.

Figure 23:
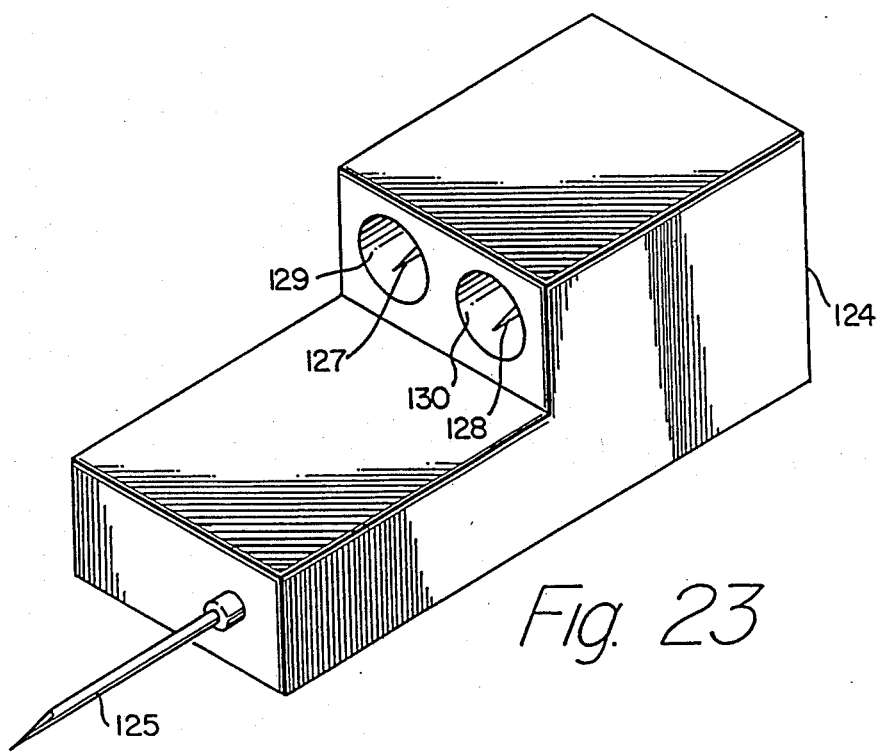
FIG. 23 is a perspective view of another alternative embodiment of the preferred device for separation of plasma from a blood sample.
Figure 24:
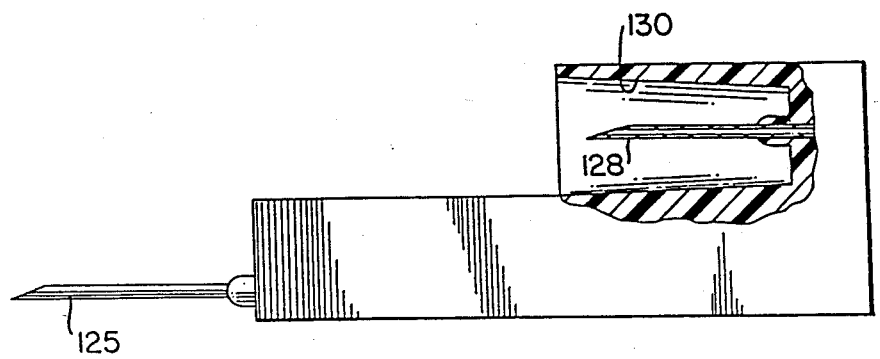
FIG. 24 is a side elevation view of the device of FIG. 23 partially cross-sectioned to illustrate the structure surrounding the second needle cannula.

Referring now to FIGS. 23 and 24, another alternative embodiment of the present device functions in substantially the same manner as the above-described preferred embodiment. This embodiment includes housing 124 having injection cannula 125, first needle cannula 127 and second needle cannula 128. This embodiment differs from previously described embodiments in that housing 124 includes frusto-conically shaped recesses 129 and 130 concentrically positioned around the first and second needle cannula, respectively. The purpose of recesses 128 and 129 is to provide a surface to guide the pierceable stopper (not shown) of the evacuated glass tube (not shown) into engagement with the needle cannula so that the needle cannula pierces the central, thinner, portion of the pierceable stopper. With the frustoconically shaped recesses functioning as a guide means for the evacuated tubes, the operator can more easily engage the evacuated tubes with the device.

Figure 25:
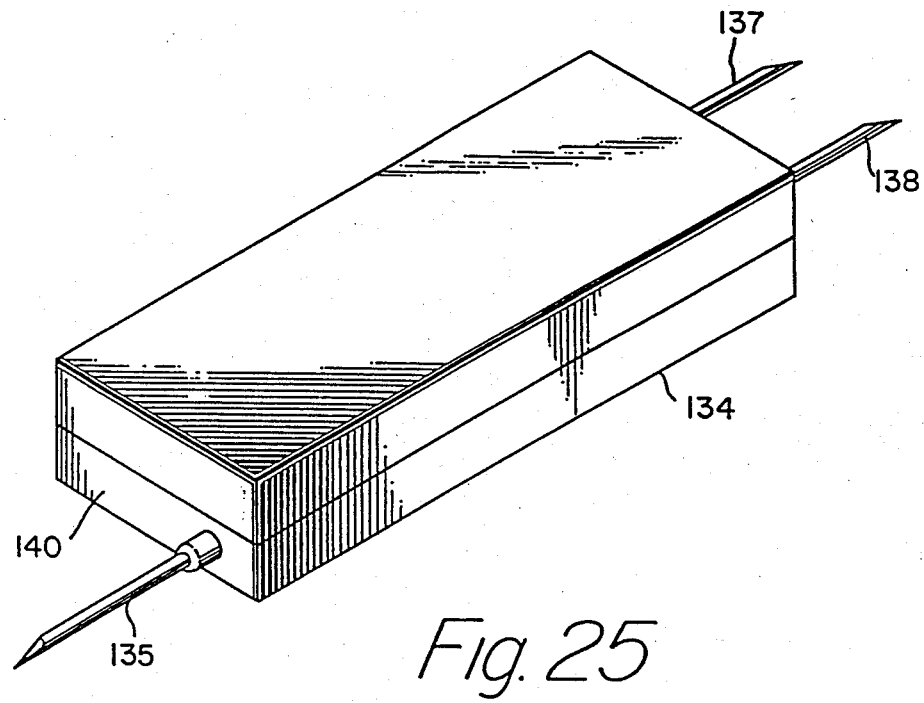
FIG. 25 is a perspective view of still another embodiment of the preferred device for separation of plasma from a blood sample.
Figure 26:
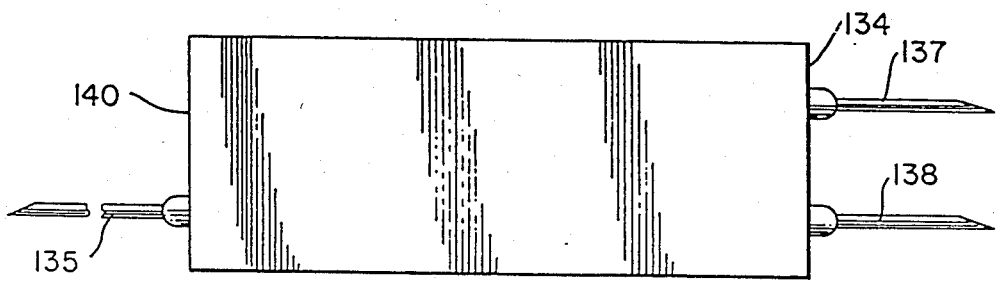
FIG. 26 is a top plan view of the device of FIG. 25.

Adverting now to FIGS. 25-26, still another alternative embodiment of the present invention includes housing 134 having injection cannula 135, first needle cannula 137 and second needle cannula 138. This embodiment functions in substantially the same manner as the embodiments described hereinabove. However, in the instant embodiment the internal configuration is altered so that the blood and plasma communication conduits are aligned so that cannula 137 and cannula 138 project outwardly from end 139 of the housing which is opposite of end 140. This embodiment illustrates that there are many possible combinations for positioning the injection cannula and the first needle cannula and the second needle cannula, and that the embodiments described herein represent only a few of the many possibilities. It is also within the purview of the present invention to include a device wherein the injection cannula and the first and second needle cannula are at or near the same end of the housing.

The housing of the present invention may be constructed of a wide variety of materials such as metals, plastics and ceramics. Plastic materials are more desirable because of their ability to be molded into a wide variety of complex shapes and for compatibility with blood. Transparent thermoplastic materials are preferred so that the operability of the device can be observed through the housing walls. A wide variety of metals and plastics are suitable for the various cannula of the present invention, with medical grade stainless steel being preferred. The choice of material for the membrane separator will depend on the composition of the materials being separated and the sizes of the particles which should be effectively blocked from passing through the membrane. Commercially available dialyzing membranes and ultrafiltration membranes may be used. Representative of such membranes are polycarbonate and polyester membranes having a pore size of within the range of between about 0.2 micron and 1.5 microns as manufactured by Nucleopore Corporation of Pleasanton, Calif., U.S.A.

First resilient sleeve 94 and second resilient sleeve 95 are preferably made of self-sealing elastomeric materials such as rubber and thermoplastic elastomers. Holding clamp 102 can be made of a wide variety of rigid materials with thermoplastic materials such as polypropylene being preferred. The use of injection molded thermoplastic, such as polypropylene, allows a design which incorporates hinge 107 as an integral part of the upper and lower portions of the holding clamp.

Thus the present invention provides a simple, straightforward, reliable, easily fabricated device for the separation of the lighter fraction from the heavier fraction of a liquid sample which will operate without the use of additional equipment such as centrifuges and pumps, to promptly produce an isolated quantity of the lighter fraction of the liquid sample. The present invention also provides greater flexibility in optimizing the efficiency of the separation process by allowing the use of two separate evacuated receptacles which may be varied as to size and degree of evacuation.

What is claimed is:

1. A method of separating the lighter fraction from the heavier fraction of a liquid sample using a device including a housing having an interior cavity, a separator membrane dividing said cavity into a first portion and a second portion, said separator membrane having a porosity selected for the desired separation thereacross, inlet means for providing fluid communication between said first portion and the source of the liquid sample, first communication means for providing fluid communication between said first portion and a first evacuated receptacle, second communication means for providing fluid communication between said second portion and a second evacuated receptacle comprising:

establishing fluid communication between said inlet means and the source of the liquid sample; and
   establishing fluid communication between a first evacuated receptacle and said first communication means and between a second evacuated receptacle and said second communication means so that the liquid sample flows through said inlet means along said membrane, through said first communication means and into said first evacuated receptacle, simultaneously, the lighter fraction of the liquid sample being drawn through said membrane and said second communication means into said second evacuated receptacle.

2. A method of separating plasma from a blood sample using a device including a housing having an interior cavity, a separator membrane dividing said cavity into a first blood receiving portion and a second plasma receiving portion, said separator membrane having a porosity selected for separating plasma from blood, inlet means for providing fluid communication between said blood receiving portion and the source of the blood sample, first communication means for providing fluid communication between said first portion and a first evacuated receptacle, second communication means for providing fluid communication between plasma receiving portion and a second evacuated receptacle comprising:

establishing fluid communication between said inlet means and the source of the blood sample; and
   establishing fluid communication between a first evacuated receptacle and said first communication means and between a second evacuated receptacle and said second communication means so that the blood sample flows through said inlet means along said membrane, through said first communication means and into said first evacuated receptacle, simultaneously, plasma being drawn through said membrane and said second communication means into said second evacuated receptacle.

3. The method of claim 2 wherein the step of establishing fluid communication between said inlet means and the source of the blood sample includes inserting a needle cannula into a patient's body so that blood is drawn directly from the patient into said inlet means.

4. A method of separating plasma from a blood sample using a first evacuated receptacle and a second evacuated receptacle comprising:

withdrawing blood from a patient;
   directing said blood, as it is being withdrawn, along the surface of a separator membrane, having a porosity selected for separating plasma from blood, and into a first evacuated receptacle; and
   simultaneously, causing plasma from said blood to be drawn through said membrane into said second evacuated receptacle.

5. A method of separating plasma from blood comprising:

withdrawing blood form a patient across the surface of a separator membrane, having a porosity selected for separating plasma from blood, and into a first evacuated receptacle; and
   simultaneously drawing plasma from said blood through said membrane into a second evacuated receptacle while said blood is being withdrawn.

* * * * *